United States Patent [19]

Kojima et al.

[11] 4,277,460
[45] Jul. 7, 1981

[54] CORTISOL RADIOIMMUNOASSAY METHOD AND CORTISOL DERIVATIVES USEFUL THEREFOR

[75] Inventors: Masaharu Kojima; Hisao Sone, both of Fukuoka; Hiroshi Ogawa, Kashiwa; Nobuhiko Nakazawa, Urawa; Seiji Tachibana, Tokyo, all of Japan

[73] Assignee: Daiichi Radioisotope Laboratories, Ltd., Tokyo, Japan

[21] Appl. No.: 68,834

[22] Filed: Aug. 22, 1979

Related U.S. Application Data

[62] Division of Ser. No. 802,397, Jun. 1, 1977, Pat. No. 4,190,593.

[30] Foreign Application Priority Data

Jun. 1, 1976 [JP] Japan .................................. 51-63985

[51] Int. Cl.³ ...................... G01N 33/48; A61K 43/00; G01T 1/00
[52] U.S. Cl. ...................... 424/1; 23/230 B; 260/112 B; 260/397.45; 424/1.5; 424/12
[58] Field of Search .............................. 424/1, 1.5, 12; 23/230 B; 260/112 B, 397.45

[56] References Cited

U.S. PATENT DOCUMENTS

| | | | |
|---|---|---|---|
| 4,031,117 | 6/1977 | Rao | 260/397.1 |
| 4,128,629 | 12/1978 | Eldreo et al. | 424/1 |
| 4,221,725 | 9/1980 | Bernstein et al. | 424/1 |

OTHER PUBLICATIONS

Weinstein et al., Steroids, vol. 20, 1972, pp. 789–809.
Feeser et al., Steroids, Text, pp. 607 and 650.

*Primary Examiner*—Benjamin R. Padgett
*Assistant Examiner*—Christine M. Nucker
*Attorney, Agent, or Firm*—Sughrue, Rothwell, Mion, Zinn and Macpeak

[57] ABSTRACT

The cortisol compound of the formula (E)

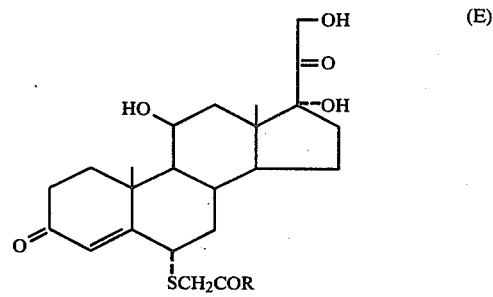

wherein R represents a hydroxy group, a tyrosine lower alkyl ester residue, a tyramine residue, a histamine residue, a 7-aminoheptanoyl-tyrosine lower alkyl ester residue, a radioiodinated tyrosine lower alkyl ester residue, a radioiodinated tyramine residue, a radioiodinated histamine residue, a radioiodinated 7-aminoheptanoyl-tyrosine lower alkyl ester residue, a protein or a polypeptide; and a radioimmunoassay method using cortisol derivative.

4 Claims, 8 Drawing Figures

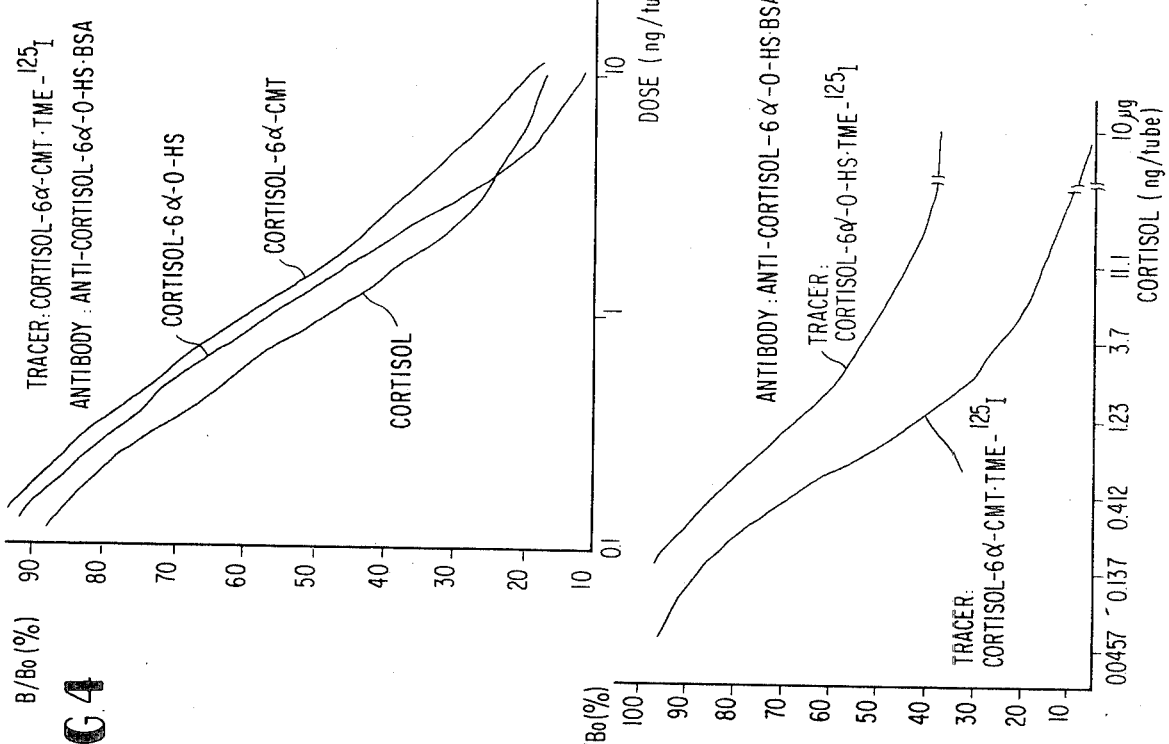

CORTISOL RADIOIMMUNOASSAY METHOD AND CORTISOL DERIVATIVES USEFUL THEREFOR

This is a division of application Ser. No. 802,397, filed June 1, 1977, now U.S. Pat. No. 4,190,593.

BACKGROUND OF THE INVENTION

1. Field of the Invention

Cortisol (i.e., 11β,17α,21-trihydroxy-4-pregnene-3,20-dione) is a steroid present in serum and urine. For the measurement of the steroid, several radioimmunoassay (hereinafter RIA) methods have been proposed and reported in, e.g., *Anal. Lett.* 5 757 (1972), ibid. 5. 767 (1972), *Journal of Analytical Endocrinology and Metabolism* 35 219 (1972), G. E. Abraham: "Radioimmunoassay of Plasma Steroid Hormones" in *Modern Methods of Steroid Analyses* Chap. 21, Academic Press, New York and London (1973), *The Japanese Journal of Nuclear Medicine* 12 123 (1975) *Clinica Chimica Acta*, 66 319-330 (1976), *Clinical and Crinology* (Tokyo) 24, 339 (1976) and the like. At the 94th Meeting of Pharmaceutical Society of Japan (Sendai, 1974), Tsuji et al proposed to produce an antibody to cortisol by injecting a cortisol-protein conjugate, i.e., cortisol-6α-O-hemisuccinate-bovine serum albumin conjugate (hereinafter, cortisol-6α-O-HS-BSA) having the formula (A)

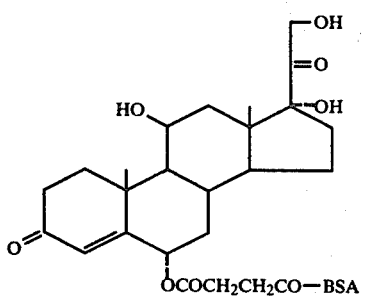

into rabbits. This proposal is described in T. Nishina, A. Tsuji and D. K. Fukushima: Steroids 24 (6) 861 (1974). This type of antigen is thought to be excellent for the production of the specific antibody because all of the functional groups of cortisol (i.e., the hydroxy groups at the 11β-, 17α- and 21-positions and the oxo groups at the 3- and 20-positions) remain free.

On the other hand, tritium($^3$H)-labeled cortisol is excellent immunologically as a tracer in RIA, but the procedure to synthesize tritium-labeled cortisol for use as a tracer is very complicated. Further measurement by counting the radioactivity should be made with a liquid scintillation counter, so that the use of such a tracer is not practical in a clinic.

As a result, investigations have now been made to prepare the conjugated compound of cortisol-6α-O-hemisuccinate with tyrosine methyl ester (i.e., cortisol-6α-O-HS-TME) having the formula (B)

and to label this compound with radioactive iodine for use as a tracer. However, when attempts were made to employ this tracer in RIA, it was found the correct standard curve was not obtained. As a result of subsequent investigations, it was found that the immunological property of the tracer were different from that of cortisol and this difference caused the inaccuracy in the standard curve. Because, two different antibodies are produced by immunization with cortisol-6α-O-hemisuccinate-BSA conjugate, i.e., an antibody to cortisol and an antibody to cortisol-6α-O-hemisuccinate (antibody to the bridge) (the hemisuccinyloxy group in formula (A) or formula (B) above is considered a "bridge"). While the immunoreaction of cortisol occurs only with the antibody to cortisol, the tracer, radioiodinated cortisol-6α-O-HS-TME, can react with the antibody to cortisol as well as with the antibody to the bridge (anti-cortisol-6α-O-hemisuccinate). Therefore, the standard curve of cortisol indicates the sum of the quantity of cortisol and the quantity of the resultant of the immunoreaction between the tracer and the antibody to the bridge. FIG. 2 and FIG. 3 of the accompanying drawings show the above relationship, in which tritium-labeled cortisol and cortisol-6α-O-HS-TME-$^{125}$I are used as a tracer, respectively. Based on the above findings, this invention has now been accomplished.

SUMMARY OF THE INVENTION

An object of this invention is to provide a new radioimmunoassay method for cortisol.

A further object of this invention is to provide cortisol derivatives useful as antigens or tracers for the radioimmunoassay of cortisol.

Another object of this invention is to provide a radioimmunoassay method in which a tracer (a labeled antigen) and an antigen for immunization (a cortisol-carrier conjugate) are used in a combination having different bridge parts.

Accordingly, in one embodiment of this invention, this invention provides a radioimmunoassay method for determining cortisol which comprises (a) immunologically producing an antibody to cortisol by injecting a cortisol-carrier conjugate having the formula (C)

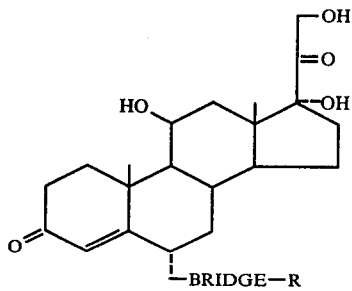

where R represents a protein or a polypeptide, and Bridge is —SCH$_2$CO— or —OCOCH$_2$CH$_2$CO—; into a host organism and producing said antibody;

(b) adding said antibody obtained in (a) and a radioactive cortisol tracer compound of the formula (D)

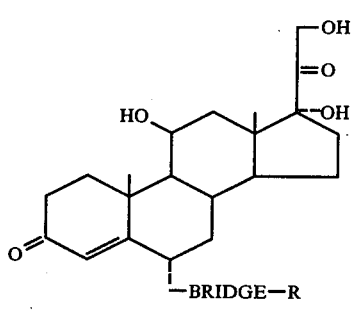

wherein R represents a radioiodinated tyrosine lower alkyl ester residue, a radioiodinated tyramine residue, a radioiodinated histamine residue, or a radioiodinated 7-aminoheptanoyltyrosine lower alkyl residue, and Bridge is —SCH$_2$CO— or —OCOCH$_2$CH$_2$CO—; to a sample containing cortisol;

(c) incubating said mixture obtained in (b);

(d) separating antibody bound tracer compound from free tracer compound; and (e) measuring the radioactivity of said antibody bound tracer compound or free tracer compound; with the proviso that said Bridge in said cortisol-carrier conjugate is different from said Bridge in said radioactive cortisol tracer compound.

In a further embodiment of this invention, the present invention provides a cortisol compound of the formula (E)

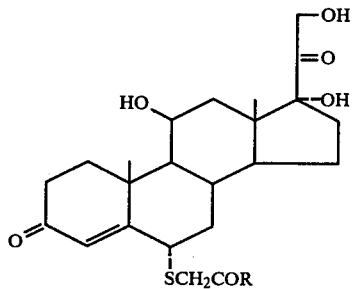

wherein R represents a hydroxy group, a tyrosine lower alkyl ester residue, a tyramine residue, a histamine residue, a 7-aminoheptanoyltyrosine lower alkyl ester residue, a radioiodinated tyrosine lower alkyl ester residue, a radioiodinated tyramine residue, a radioiodinated histamine residue, a radioiodinated 7-aminoheptanoyl-tyrosine lower alkyl ester residue, a protein or a polypeptide.

BRIEF DESCRIPTION OF THE DRAWINGS

FIGS. 2 to 8 are standard curves of RIA.

DETAILED DESCRIPTION OF THE INVENTION

Figure 1:
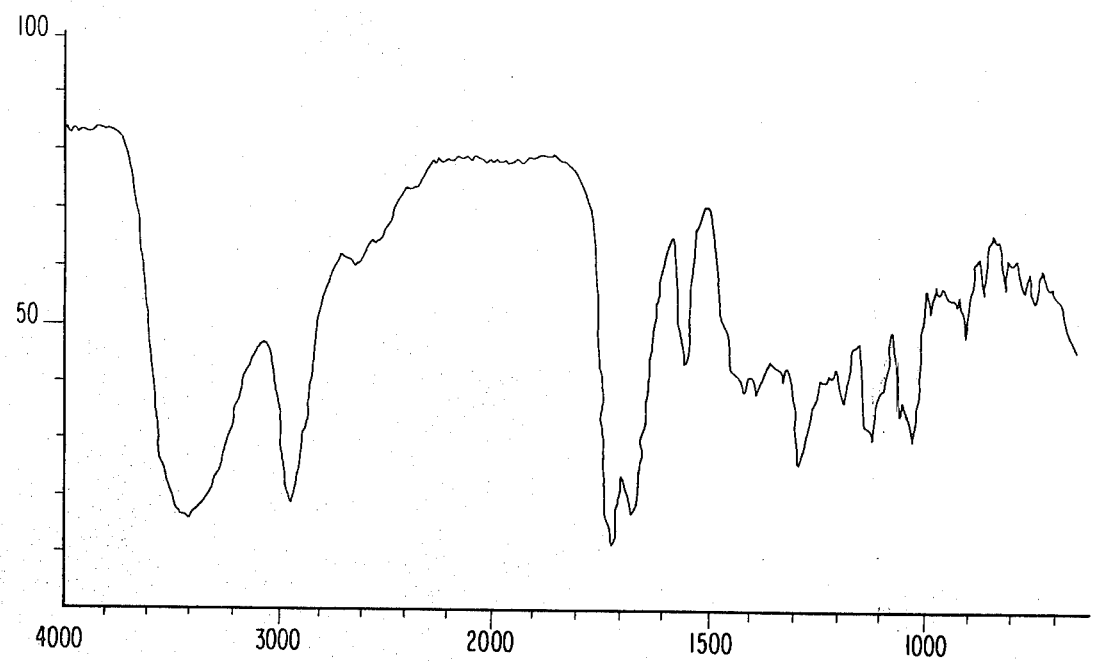
FIG. 1 is the IR spectrum of 6α-carboxymethylthiocortisol.

To conduct the RIA of cortisol using antigens having different bridge parts, this invention provides 6α-carboxymethylthiocortisol and derivatives thereof which have a novel carboxymethylthio bridge. As described herein these compounds are represented by the general formula (E-1)

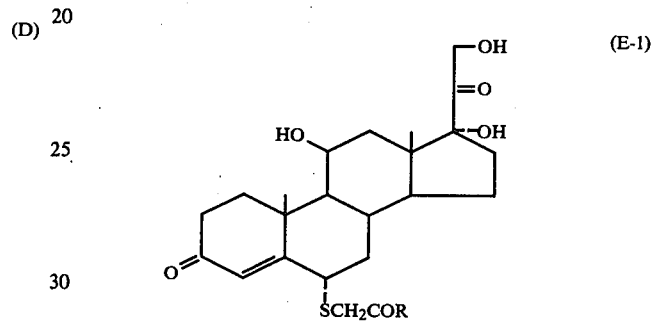

wherein R represents a hydroxyl group, an iodinated tyrosine lower alkyl ester residue in which the alkyl moiety thereof has 1 to 5 carbon atoms, an iodinated tyramine residue, an iodinated histamine residue, an iodinated 7-aminoheptanoyltyrosine lower alkyl ester residue in which the alkyl moiety therof has 1 to 5 carbon atoms or a carrier such as a protein, e.g., serum albumin, γ-globulin, thyroglobulin, etc., or a polypeptide, e.g., polylysine. Suitable examples of alkyl moieties include, e.g., a methyl moiety, an ethyl moiety, a propyl moiety, an iso-propyl moiety, an n-butyl moiety, a tert-butyl moiety, a pentyl moiety, etc. Of these compounds, 6α-carboxymethylthiocortisol(cortisol-6α-CMT) can be prepared from a known compound according to the following reaction schematic.

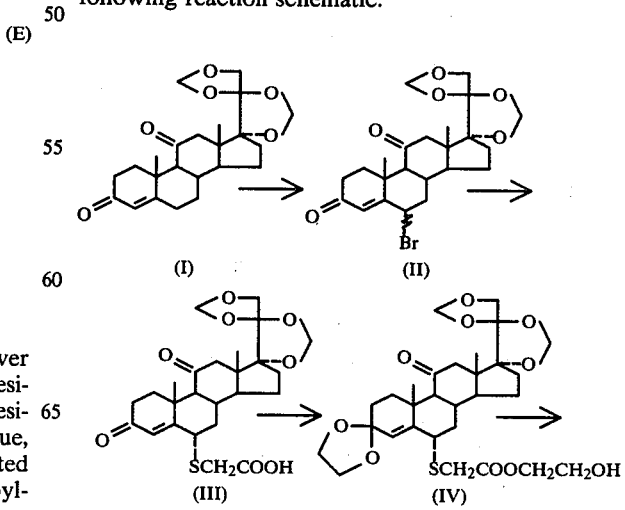

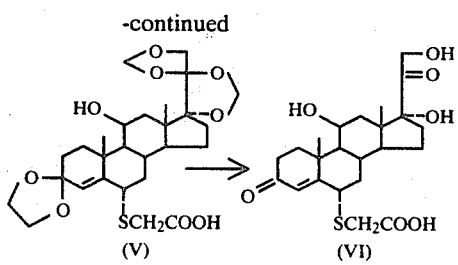

More specifically in the above reaction schematic, a known compound, 17α,20,20,21-bis-methylenedioxy-4-pregnene-3,11-dione (I) which can be prepared according to methods described in *J. Am. Chem. Soc.* 81, 1235 (1959), ibid. 82, 178 (1960), etc. is reacted with N-bromosuccinimide in an about equimolar amount [i.e., Compound (I): N-bromosuccinimide=1 g: 0.45–0.6 g] in about 40 to about 60 ml of dry benzene while heating the mixture under reflux for about 7 to about 10 hours to produce 6-bromo-17α,20,20,21-bis-methylenedioxy-4-pregnene-3,11-dione (II). Then the 6-bromosteroid (II) is mixed with thioglycolic acid ($HSCH_2COOH$) in a molar ratio about twice the amount of compound (II) and to the resulting mixture is added about 90 to about 140 ml of alkaline methanol followed by heating under reflux for about 3.5 to 4.5 hours to produce 17α,20,20,21-bis-methylenedioxy-6α-carboxymethylthio-4-pregnene-3,11-dione (III). About 5.3 g of the 3,11-dioxo compound (III) is mixed with about 200 to about 300 ml of dry benzene, about 30 to 50 ml of ethylene glycol and about 90 to about 130 mg of p-toluenesulfonic acid [about 1/20 times the amount of the compound (III)] and the mixture thus obtained is refluxed for about 18 to about 26 hours to produce 3,3-ethylenedioxy-17α,20,20,21-bis-methylenedioxy-6α-(2-hydroxyethoxy)carbonylmethylthio-4-pregnene-11-one (IV). Subsequently, the 11-oxo compound (IV) is mixed with about 8 to about 10 ml of a 10% aqueous $KCO_3$ solution and about 80 to about 120 ml of methanol and the mixture is stirred at room temperature (about 20°–30° C.) for about 26 to about 38 hrs. The hydrolysate thus obtained is concentrated and dissolved in about 15 to about 25 ml of water. To the solution is added about 35 to about 45 ml of tetrahydrofuran and about 3 to about 5 g of sodium borohydride and the resulting mixture is refluxed for about 6 to about 10 hours followed by further refluxing for about 12 to about 18 hours after about 1 to about 2 g of sodium borohydride is added to the solution and adding about 0.5 to about 1.5 g of sodium borohydride to effect reduction of the compound (IV) to produce 3,3-ethylenedioxy-17α,20,20,21-bis-methylenedioxy-6α-carboxymethylthio-4-pregene-11β-ol (V). The protective groups of compound (V) can be removed, for example, by hydrolysis, to produce 6α-carboxymethylthiocortisol (VI). The hydrolysis can be conducted, e.g., by adding a 50% aqueous acetic acid solution dropwise to about 300 mg of compound (V) until it is completely dissolved and refluxing the resulting solution for about 8 to about 10 hours.

Since compound (VI) contains a carboxyl group, various compounds containing an amino group can be conjugated thereto by an amide bond. Examples of compounds having an amino group include tyrosine, tyramine, histamine, 7-aminoheptanoyltyrosine (these compounds have a phenyl or imidazole nucleus which can be iodinated), proteins such as bovine serum albumin (BSA), rabbit serum albumin (RSA), γ-globulin or thyroglobulin or polypeptides such as polylysine.

The conjugates with proteins or polypeptides can be used for immunization of animals to produce antibodies and the conjugates with a compound having a phenyl or imidazole nucleus can be labeled with radioactive iodine (the labeled tyrosine methyl ester, tyramine histamine or 7-aminoheptanoyltyrosine methyl ester moiety is hereinafter designated the label moiety) and the labeled compound can be used as a tracer in RIA.

Conjugation may be carried out by a known reaction to form an amide bond such as a mixed anhydride method described e.g., in *J. Biol. Chem* 232 713 (1957), ibid. 234 1090 (1959), S. Lieberman et al.; *Proceedings of Progress in Hormone Research* 165 (1959), *Canad. J. Biochem. and Physiol.* 39 967 (1961), *Steroids* 24 477 (1974), etc. and the carboxyl group of, e.g., tyrosine or the like, is preferably protected with an alkyl group. The conjugation process is illustrated by the following reaction schematic using the tyrosine methyl ester as a representative example.

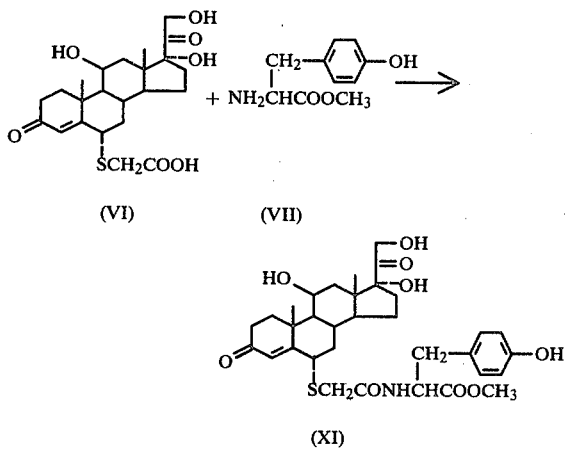

Specifically 6α-carboxymethylthiocortisol (VI), an organic amine such as n-butylamine, triethylamine, etc., and isobutyl chlorocarbonate are dissolved in an organic solvent such as tetrahydrofuran, dioxane, etc., in a molar proportion of 1: about 0.8 to about 1.2: about 0.7 to about 1.1 and the solution is allowed to stand at about −10° C. to about 10° C. for about 2 to about 5 minutes to form an anhydride of compound (VI). Then, tyrosine methyl ester is added to the solution in a molar proportion of 1: about 0.9 to about 1.3 based on compound (VI) and the mixture thus obtained is allowed to stand at about 4° to about 20° C. for about 5 min. to about 30 min. to form a conjugate (XI).

In a manner substantially the same as in the reaction schematic described above, tyramine (VIII), histamine (IX), 7-aminoheptanoyltyrosine methyl ester (X) and groups or residues other than a protein residue or a polypeptide residue can be conjugated to compound (VI). Protein residues such as BSA and polypeptides such as polylysine can be conjugated to compound (VI) in a manner similar to the reaction schematic above except that the anhydride formed and the protein or polypeptide are dissolved in water at a pH of about 8.5 to about 9.5 and reacted at about 4° C. for about 30 minutes to about 2 hours.

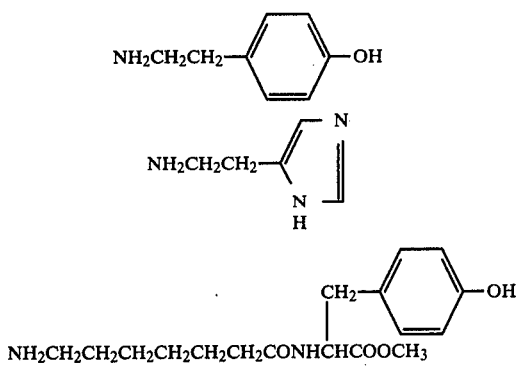

NH₂CH₂CH₂CH₂CH₂CH₂CH₂CONHCHCOOCH₃

Labeling of the conjugate such as that of formula (XI) above containing a phenyl or imidazole group can be achieved using a known method such as the method of Hunter and Greenwood Nature vol.194, page 494 (1962).

The radioactive iodine used for labeling in this invention can suitably be a radioisotope such as $^{125}I$ or $^{131}I$ and such is chosen based on the half-life thereof. That is, 0.1 to 5 μg of antigen, 20 to 50 μl of phosphate buffer (1/30–0.2 mol, pH 6.5–8), 0.5–2 milli curie of $NaI^{125}$ and 5–50 μg (i.e., 10 μl) of chloramine T is mixed and reacted at room temperature for 10 seconds to 1 minute. Thereafter, sodium metabisulfite is added to the reaction mixture in an amount 2 to 4 times the amount (by weight) of chloramine T and the resulting mixture is reacted at room temperature for 30 seconds to 2 minutes to form the labeled conjugate. Since only very small quantity of the tracer will be required for RIA, production of the tracer can be made using another method, although it is disadvantageous to carry such out on a large scale. For example, tyrosine methyl ester, tyramine, histamine or 7-aminoheptanoyltyrosine methyl ester can be labeled with radioactive iodine to prepare the label moiety beforehand and then the label moiety is reacted with the steroid of formula (VI). Labeling of tyrosine methyl ester, tyramine, histamine or 7-aminoheptanoyltyrosine methyl ester can be accomplished using the same method of Hunter and Greenwood, supra, as described above.

The tracers or intermediates thereof can be easily purified using known methods such as chromatography, for example, thin layer chromatography, and if a small quantity of the product is to be purified, using silica gel. The substances labeled with radioactive iodine have the same properties as those of the corresponding non-labeled compound except for the radioactivity. The tracers and intermediates thereof can be identified with ease by thin layer chromatography and it is conventional to use a thin layer scanner to detect the radioactive substances.

The following examples are given to illustrate in greater detail the preparation of tracers or intermediates thereof. Unless otherwise indicated herein, all parts, percents, ratios and the like are by weight.

EXAMPLE 1

(a) In 50 ml of dry benzene was dissolved 1 g of 17α,20,20,21-bis-methylenedioxy-4-pregnene-3,11-dione (I). After addition of 0.53 g of N-bromosuccinimide, the mixture was heated under reflux for 8.5 hours. The solvent was removed by distillation in vacuo and the residue was chromatographed on neutral alumina eluted with a mixture of benzene-chloroform (4:1 by volume) to obtain 0.85 g of a oily crude compound (II). The oily compound (II) was purified additionally several times and the crystals obtained were recrystallized from an acetone-petroleum ether mixture [the petroleum ether was added dropwise until crystals of compound (II) appeared] to obtain light yellowish needles with a melting point of 173°–173.5° C.

Elemental Analysis: $C_{23}H_{29}O_6Br$—Calc'd(%): C 57.49; H 6.08. Found(%): C 57.52; H 6.17.

$[\alpha]_D^{20}+11.1°$ (C=0.24 chloroform).

$IR\nu_{max}^{KBr}$ cm$^{-1}$: 1710, 1675 (C=O), 1100, 945 (C—O—C).

(b) In an alkaline methanol solution (0.8 g of potassium hydroxide dissolved in 115 methylmethanol) was dissolved 2.3 g of crude compound (II), prepared as described in (a) above. To the solution was added dropwise 0.71 ml of thioglycolic acid. The resulting mixture was heated under reflux for 4 hours and concentrated in vacuo. To the residue was added 85 ml of water. After adjusting the pH to 1 with a 10% hydrochloric acid aqueous solution, the mixture was extracted with ethyl acetate. The extract was washed with water then extracted with a 0.1 N sodium bicarbonate aqueous solution. The extract was washed with ethyl acetate and the pH of the alkaline water solution was adjusted to 1 with a 10% hydrochloric acid aqueous solution. The precipitate was extracted with ethyl acetate and the extract was dried with sodium sulfate. The solvent was removed by distillation in vacuo to obtain 1.2 g of oily compound (III). Oily compound (III) was purified using silica gel column chromatography eluting with a chloroform-methanol mixture (98:2 by volume) and recrystallized from diethyl ether to obtain colorless platelets with a melting point of 223°–225° C.

Elemental Analysis: $C_{25}H_{32}O_2S$—Calc'd(%): C 60.96; H 6.55. Found(%): C 60.94; H 6.60.

NMR(CDCl₃)δ: 0.84(3H,s,18-CH₃), 1.46(3H,s,19-CH₃), 3.42(2H,s,—S—CH₂—), 3.72(1H,d.d.,J=4 Hz,16 Hz, 16β-H).

$IR\nu_{max}^{film}$ cm$^{-1}$: 1710, 1680(C=O), 1100, 950(C—O—C).

The conformation of the carboxymethylthio group was determined to be an α bond from the NMR spectrum.

(c) In 250 ml of dry benzene was dissolved 5.3 g of crude compound (III), prepared as described in (b) above. To the solution were added 40 ml of ethylene glycol and 110 mg of p-toluenesulfonic acid. The mixture was heated under reflux for 22 hours in a system with a water separator. After reaction, the benzene layer was separated, washed with water, dried with sodium sulfate and the solvent was removed by distillation to obtain 3.4 g of oily compound (IV).

$IR\nu_{max}^{film}$ cm$^{-1}$: 3520(O—H), 1745, 1720(C=O), 1280(CO—O), 1100, 950(C—O—C).

Mass spectrum m/e: 580(M+), 535(M+-45).

(d) In 100 ml of methanol, was dissolved 0.9 g of the crude compound (IV), prepared as described in (c) above. After addition of 9 ml of a 10% potassium carbonate aqueous solution, the mixture was stirred at room temperature (about 20°–25° C.) for 32.5 hours. The solvent was removed by distillation in vacuo and the residue was dissolved in 20 ml of water and washed 3 times with diethyl ether. To the water solution were added 40 ml of tetrahydrofuran and then 4 g of sodium borohydride was added thereto. The mixture was heated under reflux while 1.5 g and 1 g of sodium borohydride were added after 8 hours and 15 hours, respectively. After the reaction was completed, the tetrahydrofuran was removed by distillation in vacuo. To the residue was added incrementally 50 ml of a 20% acetic acid aqueous solution under cooling with ice to decompose the sodium borohydride. Then the mixture was extracted with chloroform and the extract was washed several times with water and dried with sodium sulfate. The solvent was removed by distillation in vacuo to obtain 300 mg of oily compound (V).

IR$\nu_{max}^{film}$ cm$^{-1}$: 3545(O-H), 1725(C=O), 1100, 950(C—O—C).

In a 50% acetic acid aqueous solution (pretreated with nitrogen gas to remove dissolved oxygen) was dissolved 300 mg of oily compound (V) prepared as described above and the solution was heated under reflux in a nitrogen stream for 9 hours. The solvent was removed and the residue was chromatographed on silica gel eluting with a benzene-methanol mixture (9:1 by volume) to obtain 21 mg of 11β,17α,21-trihydroxy-6α-carboxymethylthio-4-pregnene-3,20-dione (VI) in the form of colorless needles.

Elemental Analysis: $C_{25}H_{32}O_7S$—Calc'd(%): C 61.04; H 7.13. Found(%): C 61.41; H 7.48.

IR$\nu_{max}^{film}$ cm$^{-1}$: 3440(O—H), 1720, 1680(C=O).

EXAMPLE 2

(a) To 30 μl of a M/30 phosphate aqueous buffer solution was added about 1 μg to tyrosine methyl ester, tyramine, histamine or 7-aminoheptanoyltyrosine methyl ester. To the mixture were added about 1 mCi of radioactive sodium iodide (Na$^{125}$I) and 10 μg of chloramine T. The reaction was conducted for 30–60 seconds and 20 μg of sodium metabisulfite was added to the mixture.

(b) To 10 μg of 6α-carboxymethylthiocortisol (VI) were added 5 μg of a tetrahydrofuran solution containing 5 nl of tri-n-butylamine, 20 μl of tetrahydrofuran and 5 μl of tetrahydrofuran solution containing 2.5 ml of isobutyl chlorocarbonate and the mixture was stirred using a vortex type mixer for 30 minutes.

(c) The reaction mixtures obtained from procedures (a) and (b) above were combined and stirred using a vortex type mixer for 15 minutes. The reaction mixture or extract thereof with ethyl acetate was purified using thin layer chromatography. That is, the reaction mixture or extract thereof was spotted on a plate of silica gel (Kiesel Gel 60 F$_{254}$; tradename produced by Merck & Co.: 6×20 cm) with blowing nitrogen gas to dry, then developed with an ethyl acetate-methanol-water mixture (85:15:1 by volume) (for iodinated histamine derivatives) or a chloroform-methanol-water mixture (9:1:0.1 by volume) (for the other compounds such as iodinated tyrosine methyl ester, iodinated tyramine or iodinated 7-aminoheptanoyltyrosine methyl ester). The spot was collected and extracted with methanol, then the extract was concentrated to dryness. The resulting residue was dissolved in a buffer solution, which was used in RIA.

The tracers and intermediates prepared were thin layer chromatographed on silica gel (kiesel Gel 60 F$_{254}$) and the Rf values obtained therefor are listed in the following table.

| Tracers & Interdemates | Rf$_1$ | Rf$_2$ | Rf$_3$ |
|---|---|---|---|
| TME-$^{125}$I | — | 0.24–0.28 | — |
| Tym-$^{125}$I | — | ca 0.00 | — |
| Him-$^{125}$I | 0.0 | 0.00–0.03 | — |
| 7-AH . TME-$^{125}$I | — | ca 0.00 | — |
| C-CMT | 0.19–0.22 | ca 0.02 | — |
| C-CMT . TME-$^{125}$I | — | ca 0.30 | 0.10 |
| C-CMT . Tym-$^{125}$I | — | 0.22–0.34 | — |
| C-CMT . Him-$^{125}$I | 0.60–0.63 | ca 0.10 | — |
| C-CMT . 7-AH . TME-$^{125}$I | — | ca 0.19 | — |
| Na$^{125}$I | 0.39–0.44 | — | — |
| C-HS . TME-$^{125}$I | — | — | 0.13–0.16 |

In the table Rf$_1$, Rf$_2$ and Rf$_3$ are the values obtained on development with an ethyl acetate-methanol-water mixture (85:15:1 by volume), a chloroform-ethyl acetate-methanol-water mixture (5:1:0.1 by volume) and a chloroform-methanol-water mixture (9:1:0.1 by volume), respectively and the abbreviations used in the table above are described below.

C-CMT: 6α-Carboxymethylthiocortisol
TME: Tyrosine methyl ester
Tym: Tyramine
Him: Histamine
7-AH: 7-Aminoheptanoyl
C-HS: Cortisol-6α-O-hemisuccinate Known methods can be used to produce the antibody to cortisol as described e.g., in *Steroids* 23 49 (1974), ibid. 23 203 (1974), etc. For example, a cortisol-carrier conjugate (1 mg) is emulsified in complete Freund's adjuvant (1:1) and injected into animals such as rabbits, goats, sheep, guinea pigs, and the like. The booster injections (0.5 mg) are made at one-month intervals for 5 to 6 months. Then the animals are bled and the serum therefrom is separated by fractionation using ammonium sulfate to obtain the IgG fraction. The IgG fraction is dialysed against a 0.002 M sodium chloride aqueous solution and used as an antibody for RIA.

The radioimmunoassay of cortisol using the antibody and the tracer described above can be conducted using a known procedure such as adsorbent methods using charcoal, Florisil, ion exchange resins and the like, non-specific precipitation (or γ-globulin precipitation) methods using saturated ammonium sulfate, polyethylene glycol, ethanol and the like, solid phase methods, double antibody methods, etc., as described in e.g., *Anal. Lett.* 5 757 (1972), ibid, 5 767 (1972), *Journal of Analytical Endocrinology and Metabolism* 35 219 (1972), G. E. Abraham; "Radioimmunoassay of Plasma Steroid Hormones" in *Modern Methods of Steroid Analyses* Chap. 21 Academic Press, New York and London (1973), *The Japanese Journal of Nuclear Medicine* 12 123 (1975) *Clinica Chimica* Acta, 66 319–330 (1976) *Clinical and Crinology* (Tokyo) 24, 339 (1976) and the like, S. G. Hillier and K. Griffith: *Steroid Immunoassay* E. H. D. Cameron, Ed. Alpha Omega Publishing Ltd., Cardiff. Wales U.K. (1975). For example, the diluted antibody (IgG fraction) in borate buffer aqueous solution, the tracer (10,000–20,000 cpm) and the standard solution (or sample) are incubated at 4° C. for 60 minutes. Dextran coated charcoal (1 ml) is then added to the resulting mixture. The mixture is stirred using a vortex type mixer, allowed to stand at 4° C. for 10 minutes and centrifuged under 2000>G for 20 minutes. The supernate is aspirated off and the radioactivity of the precipitate is counted in a conventional manner using a scintilation counter.

Figure 2:
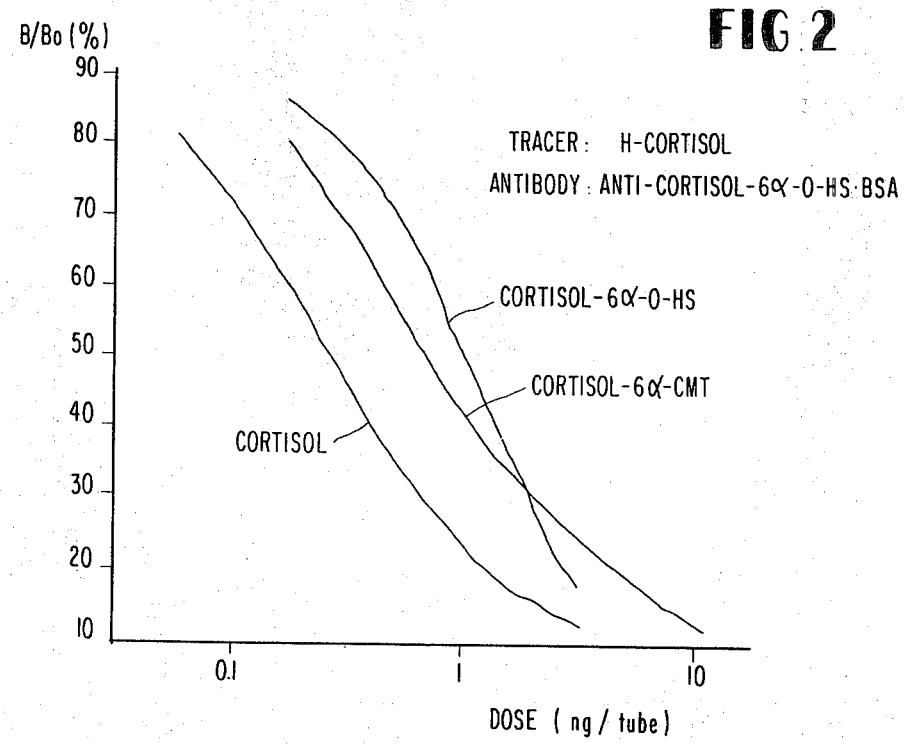
Figure 6:
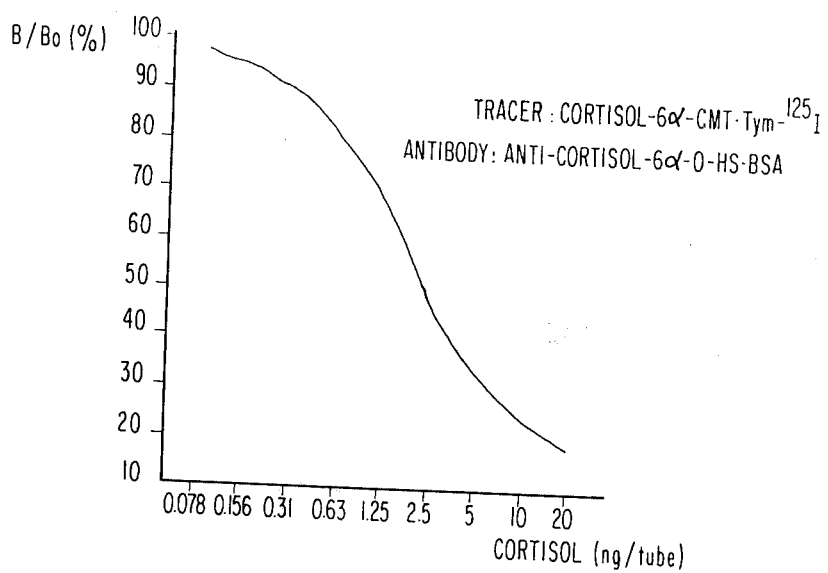
Figure 7:
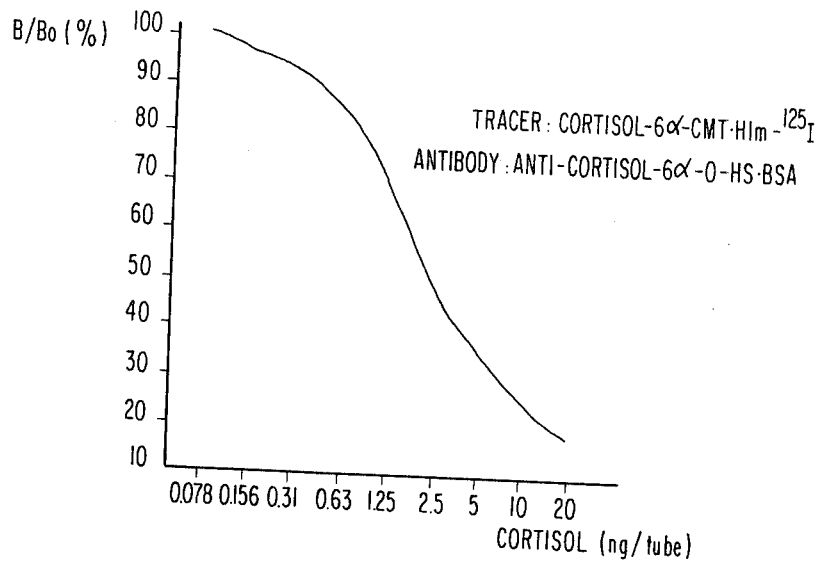
Figure 8:
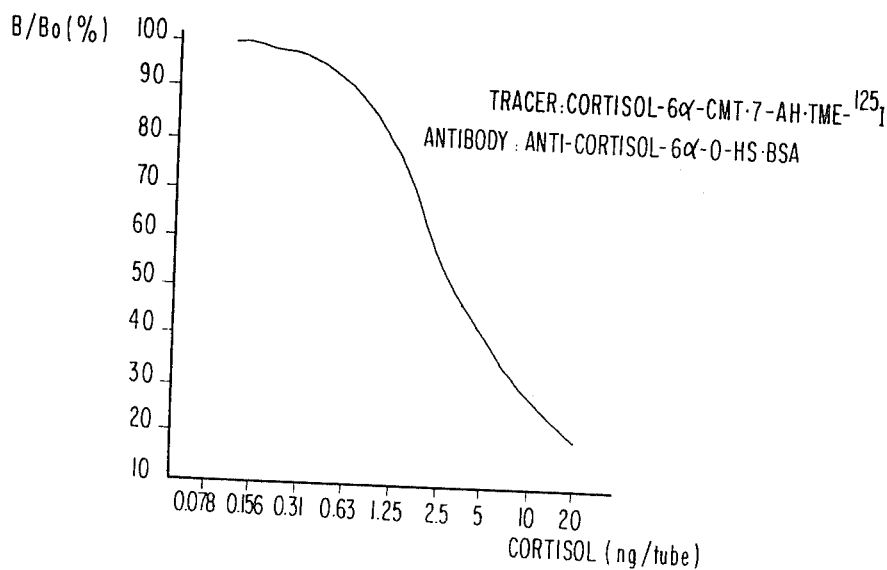

Several standard curves obtained are shown on FIGS. 2 to 8 in which anti-cortisol-6α-O-HS-BSA was used as an antibody.

As can be understood from the results presented in the figures, when the tracer had the same bridge as that of the cortisol-BSA conjugate (O-hemisuccinyl group), the standard curve of cortisol or cortisol-6α-CMT did not fall enough but became flat or substantially parallel to the horizontal axis. While not desiring to be bound, the reason for this is believed to be as follows. When even a large excess (with respect to the tracer) of the standard compound (cortisol or corsitol-6α-CMT) is reacted, the tracer is still bound with the antibody (which is thought to be the antibody to the bridge) and the precipitate has considerable radioactivity (see the curve of cortisol and that of cortisol-6α-CMT in FIG. 3; see the curve of cortisol-6α-HS-TME-$^{125}$I in FIG. 5). However, when the tracer had a different bridge (a carboxymethyl thio group) from that of the cortisol-BSA conjugate, the standard curve fell sufficiently with a large dose of the standard compound. Thus, the introduction of a different bridge into the tracer causes the standard curve to be more sensitive.

In the above explanation, cortisol-6α-O-hemiscuccinate-BSA conjugate is used as an antigen for antibody production. However, 6α-carboxymethylthiocortisol-BSA conjugate can be used as an antigen for producing an antibody as well, and in this case the tracer should have a different bridge such as a hemisuccinyloxy group.

While the invention has been described in detail and with reference to specific embodiments thereof, it will be apparent to one skilled in the art that various changes and modifications can be made therein without departing from the spirit and scope thereof.

We claim:

1. A radioimmunoassay method for determining cortisol which comprises
   (a) immunologically producing an antibody to cortisol (C) by injecting a cortisol-carrier conjugate having the formula (C)

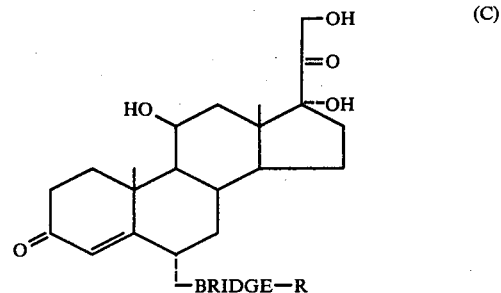

wherein R represents a protein or a polypeptide, and Bridge is —SCH$_2$CO— or —OCOCH$_2$CH$_2$CO—; into a host organism and producing said antibody;
   (b) adding said antibody obtained in (a) and a radioactive cortisol tracer compound of the formula (D)

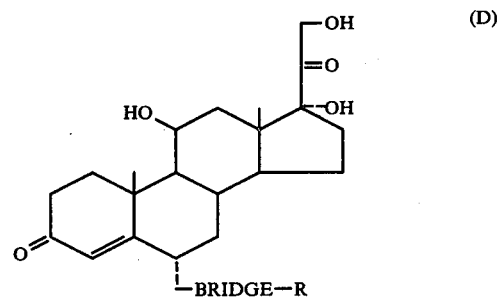

wherein R respresents a radioiodinated tyrosine lower alkyl ester residue, a radioiodinated tyramine residue, a radioiodinated histamine residue, or a radioiodinated 7-aminoheptanoyltyrosine lower alkyl residue, and Bridge is —SCH$_2$CO— or —OCOCH$_2$CH$_2$CO—; to a sample containing cortisol;
   (c) incubating said mixture obtained in (b);
   (d) separating antibody bound tracer compound formed in (c) from free tracer compound; and
   (e) measuring the radioactivity of said antibody bound or free tracer compound; with the proviso that said Bridge in said cortisol-carrier conjugate is different from said Bridge in said radioactive cortisol tracer compound.

2. The method of claim 1, wherein the bridge is selected from the group consisting of hemisuccinyloxy and carboxymethylthio.

3. The method of claim 1, wherein the bridge of said radioactive cortisol tracer compound is carboxymethylthio and the bridge of said cortisol-carrier conjugate is hemisuccinyloxy.

4. The method of claim 1, wherein said protein is serum albumin, γ-globulin or thyroglobulin and said polypeptide is polylysine.